(12) United States Patent
Wang et al.

(10) Patent No.: US 9,040,705 B2
(45) Date of Patent: *May 26, 2015

(54) PREPARATION OF SATURATED KETONE MORPHINAN COMPOUNDS

(75) Inventors: Peter X. Wang, Creve Coeur, MO (US); Tao Jiang, Chesterfield, MO (US); Narayanasamy Gurusamy, Ballwin, MO (US); Catherine K. Jung, Skokie, IL (US)

(73) Assignee: Mallinckrodt LLC, Hazelwood, MO (US)

( * ) Notice: Subject to any disclaimer, the term of this patent is extended or adjusted under 35 U.S.C. 154(b) by 539 days.

This patent is subject to a terminal disclaimer.

(21) Appl. No.: 12/757,098

(22) Filed: Apr. 9, 2010

(65) Prior Publication Data

US 2010/0261907 A1 Oct. 14, 2010

Related U.S. Application Data

(60) Provisional application No. 61/247,019, filed on Sep. 30, 2009, provisional application No. 61/167,876, filed on Apr. 9, 2009.

(51) Int. Cl.
*C07D 489/02* (2006.01)
*C07D 489/04* (2006.01)

(52) U.S. Cl.
CPC ............ *C07D 489/04* (2013.01); *C07D 489/02* (2013.01)

(58) Field of Classification Search
None
See application file for complete search history.

(56) References Cited

U.S. PATENT DOCUMENTS

| | | | |
|---|---|---|---|
| 2,544,291 | A | 3/1951 | Baizer |
| 2,577,947 | A | 12/1951 | Baizer et al. |
| 2,628,962 | A | 2/1953 | Homeyer et al. |
| 2,649,454 | A | 2/1953 | Rapoport |
| 2,654,756 | A | 10/1953 | Homeyer et al. |
| 2,715,626 | A | 8/1955 | Pfister, III |
| 5,571,685 | A | 11/1996 | Hailes et al. |
| 5,847,142 | A | 12/1998 | Mudryk et al. |
| 6,589,960 | B2 | 7/2003 | Harclerode et al. |
| 7,321,038 | B2 | 1/2008 | Wang et al. |
| 7,323,565 | B2 | 1/2008 | Wang et al. |
| 7,399,038 | B2 | 7/2008 | Vandewinckel et al. |
| 7,399,858 | B2 * | 7/2008 | Wang et al. ............... 546/45 |
| 7,399,859 | B1 | 7/2008 | Kouznetsov |
| 2006/0155130 | A1 | 7/2006 | Wang et al. |

FOREIGN PATENT DOCUMENTS

| | | |
|---|---|---|
| DE | 365683 | 12/1922 |
| DE | 415097 | 6/1925 |
| DE | 607931 | 1/1935 |
| DE | 617238 | 2/1935 |
| DE | 623821 | 2/1936 |
| WO | WO 2005/047291 | 5/2005 |
| WO | WO2005/100361 | * 10/2005 |
| WO | WO 2005/100361 | 10/2005 |

OTHER PUBLICATIONS

Indiana, physical properties of amine, Mar. 2010, p. 1-8. (powerpoint presentation).*
Kalinin et al. Palladium-Catalyzed 2-Phenylethenylation of Codeine: 8-[(1E)-2-Phenylethenyl]codeinone Dimethyl Ketal as the Unexpected 'Masked' Diene for the Preparation of 19-Substituted Diels—Alder Adducts of Thebaine. Helvetica Chimica Acta, 2006, 89, 861-869.*
Grant & Hackh's Chemical Dictionary (5th Ed. 1987) at p. 148.*
Rapoport et al., "The Preparation of Some Dihydro Ketones in the Morphine Series by Oppenauer Oxidation", J.Org. Chem., 15, 1950, pp. 1103-1107.
Baizer et al., "The Rearrangement of codeing to Dihydrocodeinone", J. Am. Pharm. Assoc., 40, 1950, pp. 580-582.
Rimland et al., "Synthesis of $N$-[Methyl-$^{11}$C]Hydromorphone by Using Multivariate Strategies for Optimization of Radiochemical Yields", Appl. Radiat. Isot., 38, 1987, p. 651.
"Inorganic chemistry", The Condensed Chemical Dictionary, 10th ed., 1981, p. 562.
"Organic chemistry", The Condensed Chemical Dictionary, 10th ed., 1981, p. 761-762.
Mannieh, Mittdung aus dem pharmazeutiech-chemischen Laboratorium der Universitat Frankfurt a. M., Arch. Pharm. 258, 1920, pp. 295-316, (English abstract only).
Takagi, Ueber die elektrolytische Reduktion des Morphins and des Kodeins, J. Pharm. Soc. Japan, 56, 1936, pp. 44-53, (English abstract only).
Nakamura, Phenylpseudokodein, J. Pharm. Soc. Japan, 72, 1942, pp. 347-351, (English abstract only).

* cited by examiner

*Primary Examiner* — Michael Barker
*Assistant Examiner* — Po-Chih Chen

(57) ABSTRACT

The present invention provides processes for the preparation of saturated ketone morphinan compounds. In particular, the invention provides processes for the conversion of a morphinan comprising an allyl alcohol ring moiety into a morphinan comprising a saturated ketone ring moiety by an isomerization reaction catalyzed by an inorganic salt of a late transition metal.

23 Claims, No Drawings

PREPARATION OF SATURATED KETONE MORPHINAN COMPOUNDS

CROSS REFERENCE TO RELATED APPLICATIONS

This application claims the benefit of U.S. Provisional Application No. 61/247,019 filed Sep. 30, 2009, and U.S. Provisional Application No. 61/167,876 filed Apr. 9, 2009, both of which are incorporated herein in their entirety.

FIELD OF THE INVENTION

The present invention generally relates to the preparation of saturated ketone morphinan compounds. In particular, the invention relate to the use of inorganic salts of late transition metals to catalytically isomerize a morphinan comprising an allyl alcohol ring moiety into a morphinan comprising a saturated ketone ring moiety.

BACKGROUND OF THE INVENTION

Hydromorphone and hydrocodone are opioid analgesic drugs available in the market and both are generally used for relief of moderate to severe pain in patients where an opioid analgesic is appropriate. Hydrocodone is the most frequently prescribed opiate in the United States. Although hydromorphone is two to three times more potent than hydrocodone, it is also at least two to four times more expensive than hydrocodone. The higher cost of hydromorphone is due to the difficulty of its production. Despite this, however, prescriptions for hydromorphone products increased from about 0.47 million in 1998 to about 1.83 million in 2006. The aggregate production quota for hydromorphone as established by DEA increased from 766 kilograms in 1998 to 3,300 kilograms in 2006.

One of the current methods for the production of hydromorphone or hydrocodone involves a two-step oxidation/reduction route from morphine or codeine, respectively. This method, however, is expensive, low yielding, and forms impurities that are difficult to remove. Another production method involves a one-step process in which transition metal complexes are used as catalysts, but these catalysts tend to be air sensitive and/or expensive to produce. Moreover, the reactions are conducted in organic solutions because the starting material is morphine base or codeine base. Thus, there is a need for new processes for producing hydromorphone or hydrocodone at lower costs, with higher yields and higher purity to meet the increasing demand for these analgesics.

SUMMARY OF THE INVENTION

Among the various aspects of the present invention is the provision of processes for the preparation of saturated ketone morphinans by one-step isomerization reactions catalyzed by inorganic salts of late transition metals.

One aspect of the invention encompasses a process for the preparation of a morphinan comprising a saturated ketone ring moiety. The process comprises contacting a morphinan comprising an allyl alcohol ring moiety with an inorganic salt of a late transition metal such that the allyl alcohol ring moiety is catalytically isomerized to the saturated ketone ring moiety.

Another aspect of the invention provides a process for the preparation of a compound comprising Formula (III). The process comprises contacting a compound comprising Formula (II) with an inorganic salt of a late transition metal catalyst to form the compound comprising Formula (III):

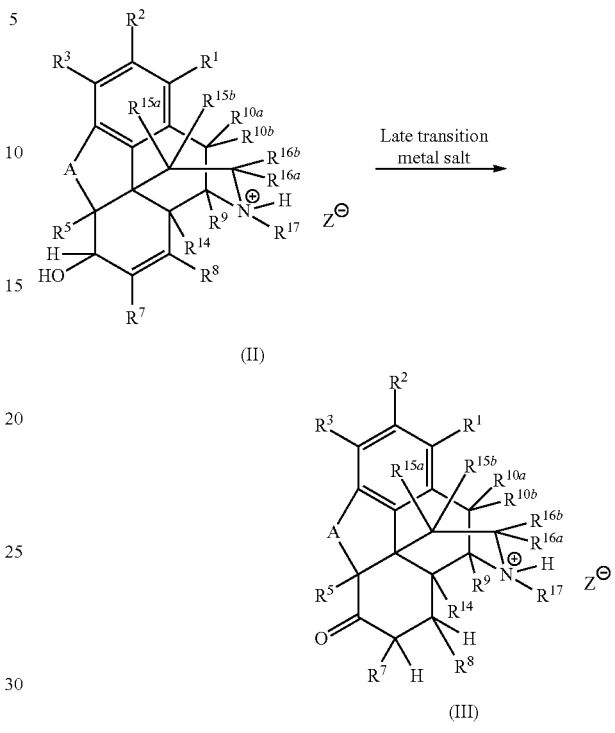

wherein:

A is a heteroatom selected the group consisting of oxygen and sulfur;

$R^1$, $R^2$, and $R^3$ are independently selected from the group consisting of hydrogen, halogen, hydroxy, protected hydroxy, {—}SH, {—}SR$^{1611}$, {—}OR$^{1611}$, and {—}NR$^{1611}$R$^{1612}$, hydrocarbyl, and substituted hydrocarbyl;

$R^5$, $R^7$, $R^8$, $R^9$, $R^{10a}$, $R^{10b}$, $R^{14}$, $R^{15a}$, $R^{15b}$, $R^{16a}$, $R^{16b}$, and $R^{17}$ are independently selected from the group consisting of hydrogen, halogen, hydroxy, {—}SH, {—}SR$^{1611}$, {—}OR$^{1611}$, and {—}NR$^{1611}$R$^{1612}$, hydrocarbyl, and substituted hydrocarbyl; provided that any of $R^{10a}$ and $R^{10b}$, $R^{15a}$ and $R^{15b}$, and $R^{16a}$ and $R^{16b}$ may together form a moiety selected from the group consisting of {=}O, {=}S, and {=}NR$^{1613}$;

$R^{1611}$, $R^{1612}$, and $R^{1613}$ are independently selected from the group consisting of hydrocarbyl, and substituted hydrocarbyl; and one or more of $R^1$, $R^2$, $R^3$, $R^5$, $R^7$, $R^8$, $R^9$, $R^{10a}$, $R^{10b}$, $R^{14}$, $R^{15a}$, $R^{15b}$, $R^{16a}$, and $R^{16b}$ may form part of a ring or ring system selected from the group consisting of carbocyclic, heterocyclic, aryl, heteroaryl, and combinations thereof; and Z is an anion.

Other aspects and features of the invention are detailed below.

DETAILED DESCRIPTION OF THE INVENTION

The present invention provides efficient one-pot processes for the catalytic rearrangement of a morphinan comprising an allyl alcohol ring moiety into a morphinan comprising a saturated ketone ring moiety, wherein an inorganic salt of a late transition metal catalyzes the isomerization. Late transition metal inorganic salts are not only efficient catalysts but also are very stable and readily available at low costs. Thus, the present invention provides cost effective processes for the preparation of saturated ketone ring-containing morphinans of high purity and excellent yields. In exemplary embodiments, the processes of the invention may be used to catalytically convert morphine or codeine into hydromorphone or hydrocodone, respectively.

Processes for the Preparation of Morphinans Comprising Saturated Ketone Ring Moieties One aspect of the present invention encompasses a process for the preparation of a saturated ketone morphinan compound comprising Formula (III). The process comprises contacting an allyl alcohol morphinan compound comprising Formula (II) with an inorganic salt of a late transition metal, wherein the compound comprising Formula (II) undergoes a double bond isomerization to form the compound comprising Formula (III). For the purposes of illustration, Reaction Scheme 1 depicts preparation of the compound comprising Formula (III) according to this aspect of the invention:

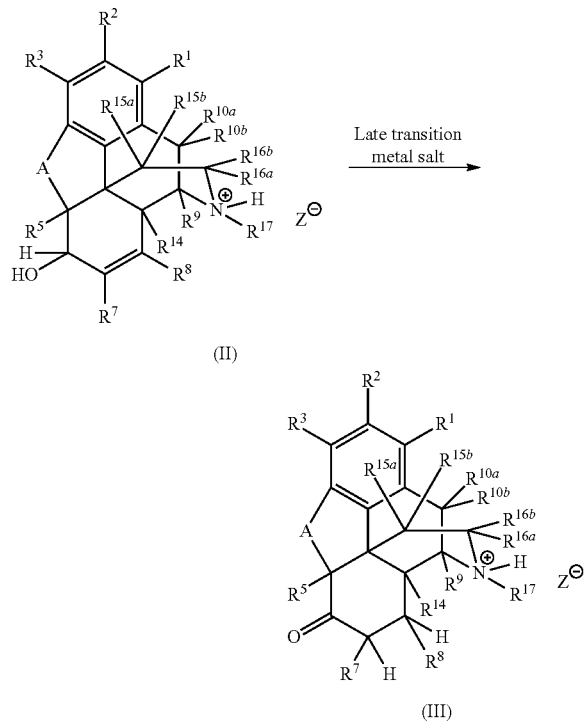

wherein:
A is a heteroatom selected the group consisting of oxygen and sulfur;
$R^1$, $R^2$, and $R^3$ are independently selected from the group consisting of hydrogen, halogen, hydroxy, protected hydroxy, {—}SH, {—}$SR^{1611}$, {—}$OR^{1611}$, and {—}$NR^{1611}R^{1612}$, hydrocarbyl, and substituted hydrocarbyl;
$R^5$, $R^7$, $R^8$, $R^9$, $R^{10a}$, $R^{10b}$, $R^{14}$, $R^{15a}$, $R^{15b}$, $R^{16a}$, $R^{16b}$, and $R^{17}$ are independently selected from the group consisting of hydrogen, halogen, hydroxy, {—}SH, {—}$SR^{1611}$, and {—}$NR^{1611}R^{1612}$, hydrocarbyl, and substituted hydrocarbyl; provided that any of $R^{10a}$ and $R^{10b}$, $R^{15a}$ and $R^{15b}$, and $R^{16a}$ and $R^{16b}$ may together form a moiety selected from the group consisting of {=}O, {=}S, and {=}$NR^{1613}$;
$R^{1611}$, $R^{1612}$, and $R^{1613}$ are independently selected from the group consisting of hydrocarbyl, and substituted hydrocarbyl;
one or more of $R^1$, $R^2$, $R^3$, $R^5$, $R^7$, $R^8$, $R^9$, $R^{10a}$, $R^{10b}$, $R^{14}$, $R^{15a}$, $R^{15b}$, $R^{16a}$, and $R^{16b}$ may form part of a ring or ring system selected from the group consisting of carbocyclic, heterocyclic, aryl, heteroaryl, and combinations thereof; and
Z is an anion.

In a preferred embodiment, A is oxygen. In another preferred embodiment, each of $R^1$, $R^2$, $R^5$, $R^7$, $R^8$, $R^9$, $R^{10a}$, $R^{10b}$, $R^{15a}$, $R^{15b}$, $R^{16a}$, and $R^{16b}$ is hydrogen. In still another preferred embodiment, $R^3$ is selected from the group consisting of hydroxy, protected hydroxy, alkyloxy, and acyloxy. In yet another preferred embodiment, $R^{17}$ is selected from the group consisting of hydrogen, alkyl, cycloalkyl, cycloalkylmethyl, allyl, and aryl. In a further preferred embodiment, $R^{14}$ is hydrogen or hydroxy.

In preferred embodiments, Z is selected from the group consisting of acetate, aspartate, benzoate, bitartrate, citrate, formate, gluconate, glucuronate, glutamate, fumarate, hydrochloride, hydrobromide, hydroiodide, hypophosphite, isobutyrate, isocitrate, lactate, malate, maleate, meconate, methanesulfonate, monohydrate, mucate, nitrate, oxalate, phenylpropionate, phosphate, phthalate, propionate, pyruvate, salicylate, stearate, succinate, sulfate, tannate, tartrate, terephthalate, valerate, and the like. In exemplary embodiments, Z is sulfate, hydrochloride, or bitartrate.

In exemplary embodiments, A is oxygen; each of $R^1$, $R^2$, $R^5$, $R^7$, $R^8$, $R^9$, $R^{10a}$, $R^{10b}$, $R^{15a}$, $R^{15b}$, $R^{16a}$, and $R^{16b}$ is hydrogen; $R^3$ is hydroxy or methoxy; $R^{14}$ is hydrogen; $R^{17}$ is methyl; and Z is sulfate, hydrochloride, or bitartrate.

(a) Reaction Mixture

The process commences with formation of a reaction mixture. In general, the reaction mixture comprises the substrate, a catalyst, and a solvent. Typically, the substrate is the compound comprising Formula (II). That is, the substrate is a pharmaceutically acceptable salt of a morphinan comprising an allyl alcohol ring moiety. In some embodiments, however, the pharmaceutically acceptable salt of the morphinan comprising an allyl alcohol ring moiety may be formed in situ by contact between the free base of a morphinan comprising an allyl alcohol ring moiety and an appropriate acid. Specifically, the free base of a morphinan comprising an allyl alcohol ring moiety is a compound comprising Formula (I):

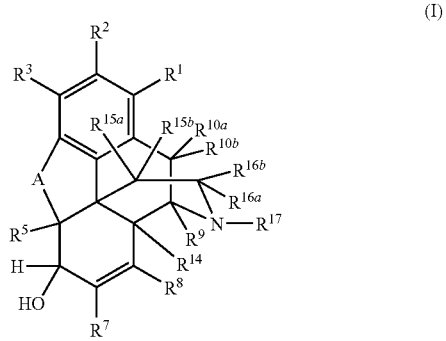

wherein:

R¹, R², R³, R⁵, R⁷, R⁸, R⁹, R¹⁰ᵃ, R¹⁰ᵇ, R¹⁴, R¹⁵ᵃ, R¹⁵ᵇ, R¹⁶ᵃ, R¹⁶ᵇ, and R¹⁷ are as defined above in Reaction Scheme 1.

The compound comprising Formula (I) may be converted into a salt by contact with an inorganic acid or an organic acid. In general, the acid is a pharmaceutically acceptable acid. Non-limiting examples of suitable inorganic acids include hydrochloric, hydrobromic, hydroiodic, nitric, carbonic, sulfuric, and phosphoric acid. Appropriate organic acids include, but are not limited to, aliphatic, cycloaliphatic, aromatic, araliphatic, heterocyclic, carboxylic, and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, hydroxybutyric, salicylic, galactaric, and galacturonic acid. In exemplary embodiments, the pharmaceutically acceptable acid may be sulfuric acid, hydrochloric acid, or tartaric acid.

Typically, an equimolar amount of the pharmaceutically acceptable acid will be contacted with the compound comprising Formula (I) such that the compound comprising Formula (II) will be formed.

(i) Catalyst

The reaction mixture also comprises the catalyst, which is an inorganic salt of a late transition metal catalyst. Preferably the late transition metal is a group VIIIB transition metal selected from the group consisting of ruthenium, rhodium, palladium, osmium, iridium, and platinum. In exemplary embodiments, the late transition metal may be ruthenium or rhodium. Those of skill in the art will appreciate that the valence of the late transition metal may vary.

The late transition metal may be complexed with a variety of inorganic anions to form an inorganic salt. Examples of suitable inorganic anions include, but are not limited to, halides, sulfates, phosphates, and nitrates. In preferred embodiments, the late transition metal inorganic salt may be $RuCl_3$, $RuBr_3$, $Ru(CF_3SO_3)_2$, $Ru_2(SO_4)_3$, $Ru(NO_3)_3$, $RhCl_3$, $RhBr_3$, $Rh_2(SO_4)_3$, $[Rh(CO_2)Cl]_2$, $IrCl_3$, $OsCl_3$, or $PdCl_2$. In an exemplary embodiment, the late transition metal salt may be $RuCl_3$.

The weight:weight ratio of the compound comprising Formula (II) to the late transition metal salt can and will vary. In general, the weight:weight ratio of the compound comprising Formula (II) to the late transition metal salt may range from about 1:0.0001 to about 1:0.1. In various embodiments, the weight:weight ratio of the compound comprising Formula (II) to the late transition metal salt may range from about 1:0.0001 to about 1:0.001, from about 1:0.001 to about 1:0.01, or from about 1:0.01 to about 1:0.1. In preferred embodiments, the weight:weight ratio of the compound comprising Formula (II) to the late transition metal salt may range from about 1:0.005 to about 1:0.04. In an exemplary embodiment, the weight:weight ratio of the compound comprising Formula (II) to the late transition metal salt may range form about 1:0.01 to about 1:0.02.

(ii) Solvent

The reaction mixture also comprises a protic solvent. Non-limiting examples of suitable protic solvents include methanol, ethanol, isopropanol, n-propanol, isobutanol, n-butanol, s-butanol, t-butanol, formic acid, acetic acid, water, and combinations thereof. In preferred embodiments, the protic solvent comprises a mixture of alcohol and water. In an exemplary embodiment, the protic solvent comprises a mixture of ethanol and water. In general, the volume:volume ratio of ethanol to water will be about 2:1.

The weight:weight ratio of the protic solvent to the compound comprising Formula (II) can and will vary. Typically, the weight:weight ratio of the protic solvent to the compound comprising Formula (II) may range from about 0.5:1 to about 10:1. In various embodiments, the weight:weight ratio of the solvent to the compound comprising Formula (II) may range from about 0.5:1 to about 2:1, from about 2:1 to about 5:1, from about 5:1 to about 10:1. In preferred embodiments, the weight:weight ratio of the solvent to the compound comprising Formula (II) may range from about 2:1 to about 4:1.

In general, the pH of the reaction mixture will be less than about pH 7. The pH of the mixture will vary depending upon, for example, the nature of the morphinan compound, the associated anion, and the catalyst. In various embodiments, the pH of the reaction mixture may be between pH 0 and 1, between pH 1 and 2, between pH 2 and 3, between pH 3 and 4, between pH 4 and 5, between pH 5 and 6, or between pH 6 and 7.

(iii) Optional Co-Reactant

In some embodiments, the reaction mixture further comprises a co-reactant. Non-limiting examples of suitable co-reactants include acetone, acetonitrile, 1-hexene, cyclohexene, $H_3PO_2$, $NaH_2PO_2$, and combinations thereof. The weight:weight ratio of the compound comprising Formula (II) to the co-reactant can and will vary. In general, the weight:weight ratio of the compound comprising Formula (II) to the co-reactant will range from about 1:0.001 to about 1:0.1. In certain embodiment, the weight:weight ratio of the compound comprising Formula (II) to the co-reactant may range from about 1:0.001 to about 1:0.01, or from about 1:0.01 to about 1:01. In a preferred embodiment, the weight:weight ratio of the compound comprising Formula (II) to the co-reactant may the co-reactant may range from about 1:0.005 to about 1:0.05.

(b) Reaction Conditions

The processes of the invention are typically performed in one step; that is, the substrate, the catalyst, the solvent, and the optional co-reactant are mixed together in a reaction vessel. The reaction is allowed to proceed at a temperature that may range from about 10° to about 120° C. In preferred embodiments, the temperature of the reaction may range from about 45° to about 100° C., or more preferably from about 65° to about 90° C. In an exemplary embodiment, the temperature of the reaction may range from about 75° to about 85° C., or more preferably from about 80° to about 85° C. In another exemplary embodiment, the temperature of the reaction may range from about 80° to about 100° C. The reaction may be conducted under ambient pressure, and preferably under an inert atmosphere (e.g., nitrogen or argon).

In general, the reaction is allowed to proceed for a sufficient period of time until the reaction is complete, as determined by any method known to one skilled in the art, such as chromatography (e.g., HPLC). Typically, the duration of the reaction will range from about 8 hours to about 24 hours. In some embodiments, the reaction may be allowed to proceed for about 8 hours, about 10 hours, about 12 hours, about 14 hours, about 16 hours, about 18 hours, about 20 hours, about 22 hours, or about 24 hours. In this context, a "completed reaction" generally means that the reaction mixture contains a significantly diminished amount of the compound comprising Formula (II) and a significantly increased amount of the compound comprising Formula (III) compared to the amounts of each present at the beginning of the reaction. Typically, the amount of the compound comprising Formula (II) remaining in the reaction mixture may be less than about 3%, less than about 1%, and preferably less than about 0.5%.

Upon completion of the reaction, the reaction mixture may be cooled and the compound comprising Formula (III) may be isolated by precipitation, filtration, distillation, phase extraction, crystallization, or other means familiar to those of skill in the art. The final product may be washed and dried, and analyzed by HPLC, UHPLC, MS, NMR, IR, or TGA.

In some embodiments, the compound comprising Formula (III) may be isolated as a free base. In particular, the product of the reaction may be isolated as a compound comprising Formula (IV):

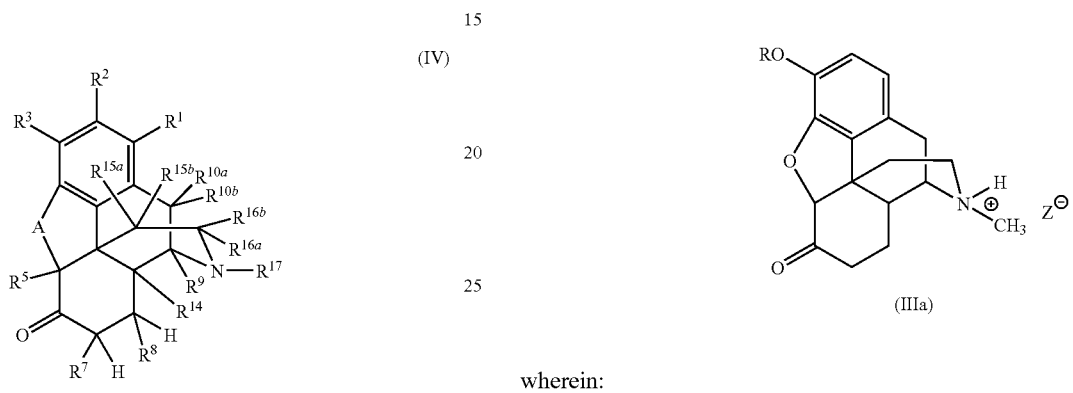

(IV)

wherein:
$R^1$, $R^2$, $R^3$, $R^5$, $R^7$, $R^8$, $R^9$, $R^{10a}$, $R^{10b}$, $R^{14}$, $R^{15a}$, $R^{15b}$, $R^{16a}$, $R^{16b}$, and $R^{17}$ are as defined above in Reaction Scheme 1.

The yield of the compound comprising Formula (III) or Formula (IV) can and will vary. Typically, the mole:mole yield of the compound comprising Formula (III) or Formula (IV) will be at least about 60%. In preferred embodiments of the invention, the mole:mole yield of the compound comprising Formula (III) or Formula (IV) may be at least about 65%, or at least about 70%. In exemplary embodiment, the mole:mole yield of the compound comprising Formula (III) or Formula (IV) may be at least about 75%, at least about 80%, or at least about 85%. In another exemplary embodiment, the mole:mole yield of the compound comprising Formula (III) or Formula (IV) may be at least about 90%, at least about 95%, at least 97%, or at least about 99%.

The compound comprising Formula (III) or Formula (IV) prepared by the processes of the invention may be an end product itself, or may be further derivatized in one or more steps to yield further intermediates or end products. Furthermore, the compound comprising Formula (IV) may be converted into a pharmaceutically acceptable salt or the compound comprising Formula (III) may be converted into a different pharmaceutically acceptable salt using techniques well known to those of skill in the art.

(c) Preferred Embodiment

In a preferred embodiment, a compound comprising Formula (IIa) is mixed with an inorganic salt of ruthenium or rhodium and a mixture of alcohol and water and heated to about 80-82° C. to yield the compound comprising Formula (IIIa). For the purpose of illustration, Reaction Scheme 2 depicts this aspect of the invention:

Reaction Scheme 2:

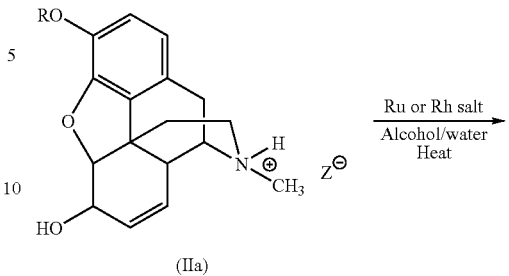

(IIa)

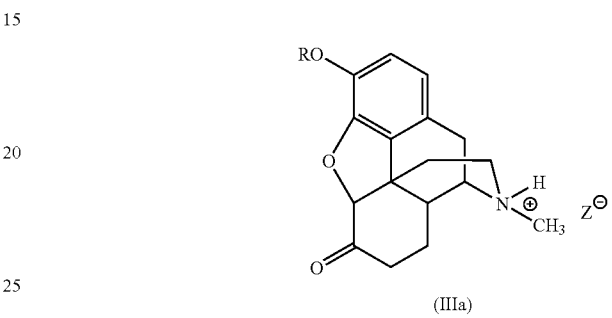

(IIIa)

wherein:
R is hydrogen or methyl.

Preferably, the weight:weight ratio of the compound comprising Formula (IIa) to the Ru or Rh salt may range from about 1:0.01 to about 1:0.2; the weight:weight ratio of the alcohol/water mixture to the compound comprising Formula (IIa) may range from about 1:1 to about 4:1; and the reaction may be conducted at a temperature from about 65° C. to about 90° C. In some embodiments, the reaction mixture further comprises a co-reactant such as acetone, acetonitrile, 1-hexene, cyclohexene, $H_3PO_2$, $NaH_2PO_2$, or combinations thereof. In one exemplary embodiment, the late transition metal salt is $RuCl_3$. In another exemplary embodiment, the solvent comprises a mixture of ethanol and water.

In some embodiments, the compound comprising Formula (IIa) may be formed in situ by contacting an acid with a compound comprising Formula (Ia):

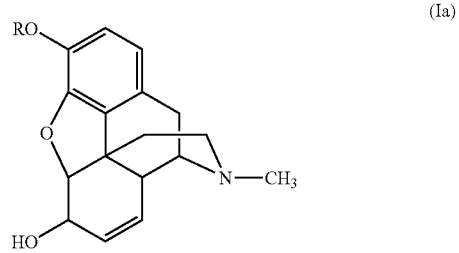

(Ia)

In additional embodiments, the compound comprising Formula (IIIa) may be isolated as a free base comprising Formula (IVa):

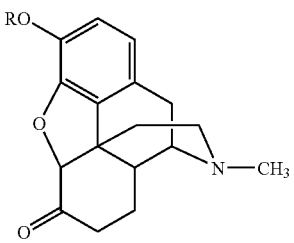

(IVa)

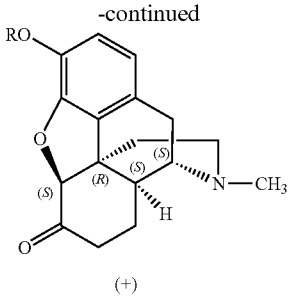

(+)

(d) Stereochemistry

The substrates and the products of the processes of the invention are morphinan compounds. For the purposes of discussion, the ring atoms of a morphinan compound are numbered as diagrammed below. Morphinan compounds have asymmetric centers. In particular, the core morphinan compound may have at least four chiral carbons (designated by asterisks); namely, C-5, C-13, C-14, and C-9.

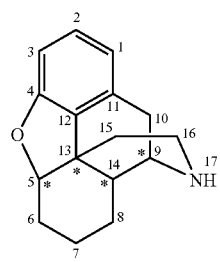 [SMILES: c1cc2c3c(c1)OC1CCCC4C(C2)NCCC314]

Any of the compounds comprising Formulas (III) or (IIIa) may have a (−) or (+) orientation with respect to the rotation of polarized light, depending upon whether the starting substrate has (−) or (+) optical activity. More specifically, each chiral center has an R or an S configuration. In particular, the configuration of the chiral carbons C-5, C-13, C-14, and C-9 may be RRRR, RRSR, RRRS, RRSS, RSRR, RSSR, RSRS, RSSS, SRRR, SRSR, SRRS, SRSS, SSRR, SSSR, SSRS, or SSSS, provided that the C-15 and the C-16 carbons are both either on the alpha face or the beta face of the molecule.

In a preferred embodiment, the compound produced by the process of the invention is a compound as diagrammed below, wherein Z is an anion. When R is hydrogen, the compound is hydromorphone, and when R is methyl, the compound is hydrocodone. In one exemplary

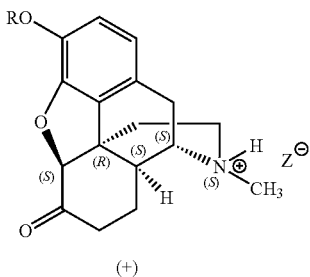

(+)

embodiment, the optical activity of the compound may be (+), and the configuration of C-5, C-13, C-14, and C-9, respectively, may be SRSS. In another exemplary embodiment, the optical activity of the compound may be (−), and the configuration of C-5, C-13, C-14, and C-9, respectively, may be RSRR.

Definitions

The compounds described herein have asymmetric centers. Compounds of the present invention containing an asymmetrically substituted atom may be isolated in optically active or racemic form. All chiral, diastereomeric, racemic forms and all geometric isomeric forms of a structure are intended, unless the specific stereochemistry or isomeric form is specifically indicated.

The term "acyl," as used herein alone or as part of another group, denotes the

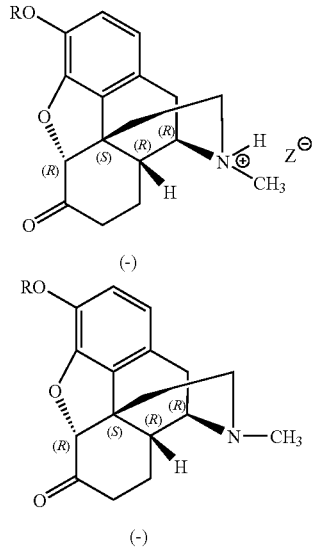

moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "protecting group" as used herein denotes a group capable of protecting an oxygen atom (and hence, forming a protected hydroxy), wherein the protecting group may be removed, subsequent to the reaction for which protection is employed, without disturbing the remainder of the molecule. Exemplary protecting groups include ethers (e.g., allyl, triphenylmethyl (trityl or Tr), p-methoxybenzyl (PMB), p-methoxyphenyl (PMP)), acetals (e.g., methoxymethyl (MOM), β-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)), esters (e.g., benzoate (Bz), allyl carbonate, 2,2,2-trichloroethyl carbonate (Trac), 2-trimethylsilylethyl carbonate), silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS) and the like. A variety of protecting groups and the synthesis thereof may be found in "Protective Groups in Organic Synthesis" by T. W. Greene and P. G. M. Wuts, John Wiley & Sons, 1999.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples illustrate various embodiments of the invention.

Example 1

One-Pot Conversion of Morphine Sulfate to Hydromorphone Sulfate—Trial 1

A reaction flask was charged with morphine sulfate (40.0 g), water (30 mL), and EtOH (60 mL). The reaction mixture was agitated to form a suspension. The reactor was flushed with nitrogen and the reaction mixture was kept under nitrogen throughout the reaction. The flask was charged with acetone (0.4 mL) and the catalyst (RuCl$_3$.xH$_2$O, 0.60 g). The reaction mixture was heated to reflux (80-82° C.) and maintained at that temperature for 24 h. HPLC analysis indicated that 93% (area) hydromorphone was formed. Acetonitrile (6 mL) was added to the reaction mixture and the mixture was heater under reflux for 2 h. EtOH (180 mL) was added to the mixture, which was then cooled down to 10° C. for 2 h. The mixture was filtered, and the solid was washed with 95% EtOH (3×15 mL). The solid was dried at 90° C. for 28 h to give 32.2 g of hydromorphone sulfate as solids (purity>98% area).

Example 2

One-Pot Conversion of Morphine Sulfate to Hydromorphone Sulfate—Trial 2

Morphine sulfate (30.0 g), water (30 mL), and EtOH (60 mL) were added to a reaction flask. The reaction mixture was agitated to form a suspension. The reactor was flushed with nitrogen and the reaction mixture was kept under nitrogen throughout the reaction. The reaction flask was charged with the catalyst (RuCl$_3$.xH$_2$O, 0.60 g), and the mixture was heated to reflux (80-82° C.) for 16 h. HPLC analysis indicated that 94.5% (area) hydromorphone was formed. Acetonitrile (30 mL) was added to the reaction mixture and the mixture was heated for 1 h. EtOH (90 mL) was added to the mixture, which was then cooled to 15° C. for 2 h. The mixture was filtered, and the solid was washed with 95% EtOH (2×15 mL). The solid was dried under vacuum at 65° C. for 18 h to give 13.8 g of hydromorphone sulfate as solids (purity>99% area).

Example 3

One-Pot Conversion of Morphine Base to Hydromorphone Sulfate—Trial 1

A reaction flask was charged with morphine base (30.0 g, wet, 75% wt, 78.85 mmol), water (23 mL), and EtOH (60 mL). The reaction mixture was agitated to form a suspension. The reactor was flushed with nitrogen and the reaction mixture was kept under nitrogen throughout the reaction. The reaction flask was charged with H$_2$SO$_4$ (98%, 7.73 g, 78.85 mmol) and the catalysts (RuCl$_3$.xH$_2$O, 0.20 g). The reaction mixture was heated to reflux (80-82° C.) for 24 h. HPLC analysis indicated that 93% (area) hydromorphone was formed. The reaction mixture was cooled down overnight. DMSO (1.0 mL) was added to the reaction mixture and the mixture was heated at reflux for 1 h. The pH of the reaction mixture was adjusted the pH to 1.6 with 50% NaOH. EtOH (90 mL) was added to the mixture, which as cooled down to 15° C. for 1 h. The mixture was filtered, and the solid was washed with 95% EtOH (2×15 mL). The solid was dried under vacuum at 65° C. for 18 h to give 11.8 g of hydromorphone sulfate as solids (purity>99% area).

Example 4

One-Pot Conversion of Morphine Base to Hydromorphone Sulfate—Trial 2

Morphine base (30.0 g, wet, 75% wt, 78.85 mmol) was dried in a vacuum oven at 90° C. for 3 h. The dried solid was added to a reaction flask, along with water (30 mL) and EtOH (60 mL). The reaction mixture was stirred to form a suspension. The reactor was flushed with nitrogen and the reaction mixture was kept under nitrogen throughout the reaction. The reaction flask was charged with H$_2$SO$_4$ (98%, 7.73 g, 78.85 mmol) and the catalyst (RuCl$_3$.xH$_2$O, 0.20 g). The reaction mixture was heated to reflux (80-82° C.) for 16 h. HPLC analysis indicated that 96.8% (area) hydromorphone was formed. The reaction mixture was cooled down overnight. Acetonitrile (30 mL) was added to the reaction mixture and the mixture was heated at reflux for 1 h. The pH of the reaction mixture was adjusted the pH to 1.6 with 50% NaOH. EtOH (90 mL) was added to the mixture, which as cooled down to 15° C. for 1 h. The mixture was filtered, and the solid was washed with 95% EtOH (2×15 mL). The solid was dried under vacuum at 65° C. for 18 h to give 11.6 g of hydromorphone sulfate as solids (purity>99% area).

Example 5

One-Pot Conversion of Codeine Base to Hydrocodone Sulfate

A reaction flask was charged with codeine base (10.0 g, 33.4 mmol), water (10 mL), and EtOH (20 mL). The reaction mixture was agitated to form a suspension. The reactor was flushed with nitrogen and the reaction mixture was kept under nitrogen throughout the reaction. The reaction flask was charged with H$_2$SO$_4$ (98%, 1.8 mL, 33.4 mmol) and the catalyst (RuCl$_3$.xH$_2$O, 0.20 g). The reaction mixture was heated to reflux (80-82° C.) for 24 h. HPLC analysis indicated that 92% (area) hydrocodone was formed. The reaction mixture was cooled down overnight. Acetonitrile (30 mL) was added to the reaction mixture and the mixture was heated for 1 h. The pH of the reaction mixture was adjusted the pH to 2.5 with 50% NaOH. EtOH (90 mL) was added to the mixture, which as cooled down to 0-5° C. for 1 h. The mixture was filtered, and the solid was washed with 95% EtOH (2×15 mL). The solid was dried under vacuum at 65° C. for 18 h to give 8.32 g of hydrocodone sulfate as solids (purity>99% area).

Examples 6-17

One-Pot Conversion of Morphine to Hydromorphone—Additional Trials

Additional trials were conducted in which the wt % of the catalyst was varied, the wt % of H$_2$SO$_4$ was varied, the presence of various co-catalysts were tested, and reaction times were varied. Table 1 lists the various reaction parameters. For each trial, a reaction flask was charged with morphine, EtOH, and water (the ratio of morphine to EtOH to water was 1 g:1.6-2 mL:0.8-1 mL). The reaction mixture was stirred and the flask was charge with catalyst (RuCl$_3$.xH$_2$O), acid (if applicable), and co-catalyst (if applicable). The reaction mixture was heated to reflux under nitrogen for the indicated period of time. The reaction was monitored by UHPLC. Upon completion of the reaction, the reaction flask was charged with anti-solvent, the pH of the mixture was adjusted, and the mixture was cooled to room temperature or 10° C. to precipitate the product. The mixture was filtered to give hydromorphone sulfate or hydromorphone base. The purity of the product was checked using orthogonal HPLC methods.

Table 1 also presents the yield and purity of the hydromorphone (HM). The reaction conditions used in Examples 6-10 and 15-17 gave yields in excess of 95% and high purity.

TABLE 1

One-Pot Formation of Hydromorphone from Morphine.

| Example | Starting material (SM) | Catalyst RuCl$_3 \cdot x$H$_2$O (Wt %) | Co-reactant Wt % to SM | H$_2$SO$_4$ to SM Wt % | Reaction time (hour) | Conversion (% area) | Purity of crude HM (% area) |
|---|---|---|---|---|---|---|---|
| 6 | Morphine sulfate | 0.5 | H$_3$PO$_2$: 0.6% Hexene-1: 4%% | 5 | 12 | 96.3 | 98.6 |
| 7 | Morphine sulfate | 0.5 | H$_3$PO$_2$: 0.6% Cyclohexene 0.8% | 5 | 12 | 97.6 | — |
| 8 | Morphine sulfate | 0.5 | H$_3$PO$_2$: 0.6% Hexene-1: 0.8% | 5 | 9 | 97.6 | — |
| 9 | Morphine sulfate | 0.5 | H$_3$PO$_2$: 0.6% | 5 | 20 | 95.8 | — |
| 10 | Morphine sulfate | 1.0 | — | 18 | 22 | 97.5 | 99.8 |
| 11 | Morphine sulfate | 1.0 | — | 0 | 20 | 93.9 | 98.9 |
| 12 | Morphine sulfate | 2.0 | — | 0 | 12 | 93.7 | 99.2 |
| 13 | Morphine sulfate | 2.0 | 1-hexene: 1.4% ACN: 0.8% | 0 | 18 | 88 | — |
| 14 | Morphine sulfate | 2.0 | 1-hexene: 1.4% Acetone: 3.2% | 0 | 16 | 92 | — |
| 15 | Morphine sulfate | 2.0 | — | 0 | 16 | 97.0 | 99.4 |
| 16 | Morphine base | 1.4 | — | 34 | 16 | 96.9 | 99.6 |
| 17 | Morphine base | 2.5 | — | 34 | 16 | 97.0 | — |

What is claimed is:

1. A one-pot process for the preparation of a morphinan comprising a saturated ketone ring moiety, the process comprising contacting a morphinan comprising an allyl alcohol ring moiety with an inorganic salt of a late transition metal in the presence of a protic solvent, wherein the allyl alcohol ring moiety is catalytically isomerized to the saturated ketone ring moiety, and wherein the weight:weight ratio of the protic solvent to the morphinan comprising an allyl alcohol ring moiety is from 2:1 to 4:1.

2. The process of claim 1, wherein the late transition metal is a group VIIIB metal selected from the group consisting of ruthenium, rhodium, palladium, osmium, iridium, and platinum; and the inorganic salt is selected from the group consisting of halide, sulfate, phosphate, and nitrate.

3. The process of claim 1, wherein the inorganic salt of the late transition metal is selected from the group consisting of RuCl$_3$, RuBr$_3$, Ru(CF$_3$SO$_3$)$_2$, Ru$_2$(SO$_4$)$_3$, Ru(NO$_3$)$_3$, RhCl$_3$, RhBr$_3$, Rh$_2$(SO$_4$)$_3$, [Rh(CO$_2$)Cl]$_2$, IrCl$_3$, OsCl$_3$, and PdCl$_2$.

4. The process of claim 1, wherein the weight:weight ratio of the protic solvent to the morphinan comprising an allyl alcohol ring moiety is from 2:1 to 3.6.

5. The process of claim 1, wherein the process comprises a single inorganic salt of a late transition metal.

6. The process of claim 1, wherein the morphinan comprising a saturated ketone ring moiety is produced with a yield in excess of 85%.

7. The process of claim 1, wherein the morphinan comprising a saturated ketone ring moiety is produced with a yield in excess of 95%.

8. A process for the preparation of a compound of Formula (III), the process comprising contacting a compound of Formula (II) with an inorganic salt of a late transition metal in the presence of a protic solvent to form the compound of Formula (III):

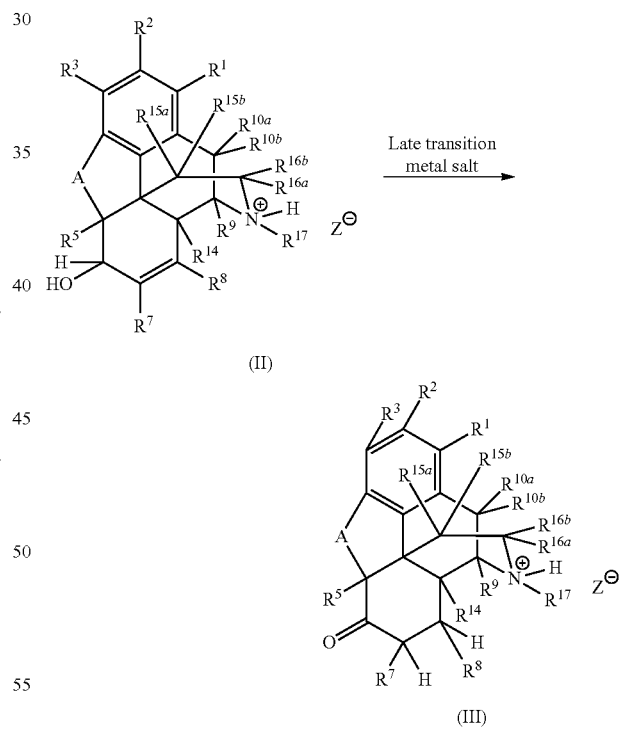

wherein:
A is a heteroatom selected from the group consisting of oxygen and sulfur;
R$^1$, R$^2$, and R$^3$ are independently selected from the group consisting of hydrogen, halogen, hydroxy, protected hydroxy, {—}SH, {—}SR$^{1611}$, {—}OR$^{1611}$, and {—}NR$^{1611}$R$^{1612}$ hydrocarbyl, and substituted hydrocarbyl;

$R^5$, $R^7$, $R^8$, $R^9$, $R^{10a}$, $R^{10b}$, $R^{14}$, $R^{15a}$ $R^{15b}$, $R^{16a}$, $R^{16b}$, and $R^{17}$ are independently selected from the group consisting of hydrogen, halogen, hydroxy, {—}SH, {-}$SR^{1611}$, {—}$OR^{1611}$, and {—}$NR^{1611}$ $R^{1612}$, hydrocarbyl, and substituted hydrocarbyl; provided that any of $R^{10a}$ and $R^{10b}$, $R^{15a}$ and $R^{15b}$, and $R^{16a}$ and $R^{16b}$ may together form a moiety selected from the group consisting of {═}O, {═}S, and {═}$NR^{1613}$;

$R^{1611}$, $R^{1612}$, and $R^{1613}$ are independently selected from the group consisting of hydrocarbyl, and substituted hydrocarbyl;

one or more of $R^1$, $R^2$, $R^3$, $R^5$, $R^7$, $R^8$, $R^9$, $R^{10a}$, $R^{10b}$, $R^{14}$, $R^{15a}$, $R^{15b}$, $R^{16a}$, and $R^{16b}$ may form part of a ring or ring system chosen from carbocyclic, heterocyclic, aryl, heteroaryl, and combinations thereof; and Z is an anion, and wherein the weight:weight ratio of the protic solvent to the compound of Formula (II) is from 2:1 to 4:1.

9. The process of claim 8, wherein A is oxygen; $R^1$, $R^2$, $R^5$, $R^7$, $R^8$, $R^9$, $R^{10a}$, $R^{10b}$, $R^{15a}$, $R^{15b}$, $R^{16a}$, and $R^{16b}$ are hydrogen; $R^3$ is selected from the group consisting of hydroxy, protected hydroxy, alkyloxy, and acyloxy; $R^{14}$ is hydrogen or hydroxy; and $R^{17}$ is selected from the group consisting of hydrogen, alkyl, cycloalkyl, cycloalkylmethyl, allyl, and aryl.

10. The process of claim 9, wherein $R^3$ is hydroxy or methyoxy; $R^{14}$ is hydrogen; $R^{17}$ is methyl; and Z is selected from the group consisting of hydrochloride, sulfate, and bitartrate.

11. The process of claim 8, wherein the compound of Formula (III) is isolated as a free base of Formula (IV):

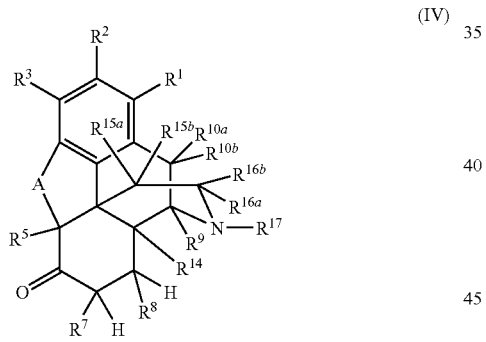

(IV)

wherein:

A is a heteroatom selected from the group consisting of oxygen and sulfur;

$R^1$, $R^2$, and $R^3$ are independently selected from the group consisting of hydrogen, halogen, hydroxy, protected hydroxy, {—}SH, {—}$SR^{1611}$, {—}$OR^{1611}$, and {—}$NR^{1611}R^{1612}$, hydrocarbyl, and substituted hydrocarbyl;

$R^5$, $R^7$, $R^8$, $R^9$, $R^{10a}$, $R^{10b}$, $R^{14}$, $R^{15a}$$R^{15b}$, $R^{16a}$, $R^{16b}$, and $R^{17}$ are independently selected from the group consisting of hydrogen, halogen, hydroxy, {—}SH, {—}$SR^{1611}$, {—}$OR^{1611}$, and {—}$NR^{1611}$ $R^{1612}$, hydrocarbyl, and substituted hydrocarbyl; provided that any of $R^{10a}$ and $R^{10b}$, $R^{15a}$ and $R^{15b}$, and $R^{16a}$ and $R^{16b}$ may together form a moiety selected from the group consisting of {═}O, {═}S, and {═}$NR^{1613}$;

$R^{1611}$, $R^{1612}$, and $R^{1613}$ are independently selected from the group consisting of hydrocarbyl, and substituted hydrocarbyl; and one or more of $R^1$, $R^2$, $R^3$, $R^5$, $R^7$, $R^8$, $R^9$, $R^{10a}$, $R^{10b}$, $R^{14}$, $R^{15a}$, $R^{15a}$, $R^{16a}$, and $R^{16b}$ may form part of a ring or ring system selected from the group consisting of carbocyclic, heterocyclic, aryl, heteroaryl, and combinations thereof.

12. The process of claim 8, wherein the compound of Formula (II) is formed in situ by contacting an acid with a compound of Formula (I):

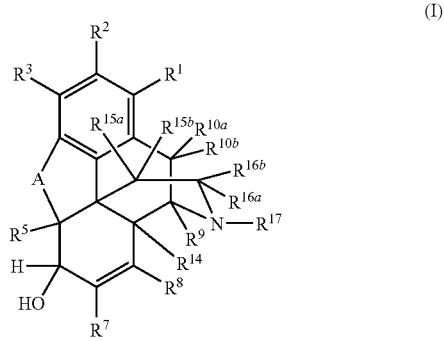

(I)

wherein:

A is a heteroatom selected from the group consisting of oxygen and sulfur;

$R^1$, $R^2$, and $R^3$ are independently selected from the group consisting of hydrogen, halogen, hydroxy, protected hydroxy, {—}SH, {—}$SR^{1611}$, {—}$OR^{1611}$ and {—}$NR^{1611}$,$R^{1612}$, hydrocarbyl, and substituted hydrocarbyl;

$R^5$, $R^7$, $R^8$, $R^9$, $R^{10a}$, $R^{10b}$, $R^{14}$, $R^{15a}$, $R^{15b}$, $R^{16a}$, $R^{16b}$, and $R^{17}$ are independently selected from the group consisting of hydrogen, halogen, hydroxy, {—}SH, {—}$SR^{1611}$, {—}$OR^{1611}$, and {—}$NR^{1611}$ $R^{1612}$, hydrocarbyl, and substituted hydrocarbyl; provided that any of $R^{10a}$ and $R^{10b}$, $R^{15a}$ and $R^{15b}$, and $R^{16a}$ and $R^{16b}$ may together form a moiety selected from the group consisting of {═}O, {═}S, and {═}$NR^{1613}$;

$R^{1611}$, $R^{1612}$, and $R^{1613}$ are independently selected from the group consisting of hydrocarbyl, and substituted hydrocarbyl; and one or more of $R^1$, $R^{b\,2}$,$R^3$, $R^5$, $R^7$, $R^8$, $R^9$, $R^{10a}$, $R^{10b}$, $R^{14}$, $R^{15a}$, $R^{15b}$, $R^{16a}$, and $R^{16b}$ may form part of a ring or ring system selected from the group consisting of carbocyclic, heterocyclic, aryl, heteroaryl, and combinations thereof.

13. The process of claim 12, wherein the acid is selected from the group consisting of sulfuric acid, hydrochloric acid, and tartaric acid.

14. The process of claim 8, wherein the late transition metal is a group VIIIB metal selected from the group consisting of ruthenium, rhodium, palladium, osmium, iridium, and platinum; and the inorganic salt is selected from the group consisting of halide, sulfate, phosphate, and nitrate.

15. The process of claim 8, wherein the inorganic salt of the late transition metal is selected from the group consisting of $RuCl_3$, $RuBr_3$, $Ru(CF_3SO_3)_2$, $Ru_2(SO_4)_3$, $Ru(NO_3)_3$, $RhCl_3$, $RhBr_3$, $Rh_2(SO_4)_3$, $[Rh(CO_2)Cl]_2$, $IrCl_3$, $OsCl_3$, and $PdCl_2$.

16. The process of claim 8, wherein the weight:weight ratio of the compound of Formula (II) to the late transition metal salt is from about 1:0.0001 to about 1:0.1; the protic solvent is selected from the group consisting of methanol, ethanol, isopropanol, n-propanol, isobutanol, n-butanol, s-butanol, t-butanol, formic acid, acetic acid, water, and combinations thereof; and the reaction is conducted at a temperature from about 10° C. to about 120° C.

17. The process of claim 16, wherein the protic solvent comprises a mixture of alcohol and water.

18. The process of claim 8, further comprising a co-reactant selected from the group consisting of acetone, acetonitrile, 1-hexene, cyclohexene, $H_3PO_2$, $NaH_2PO_2$, and combinations thereof.

19. The process of claim 8, wherein the optical activity of the compounds of Formulas (II) and (III) is (−) or (+), and the configuration of C-5, C-13, C-14, and C-9, respectively, is selected from the group consisting of RRRR, RRSR, RRRS, RRSS, RSRR, RSSR, RSRS, RSSS, SRRR, SRSR, SRRS, SRSS, SSRR, SSSR, SSRS, and SSSS, provided that the C-15 and the C-16 carbons are both either on the alpha face of the molecule or the beta face of the molecule.

20. The process of claim 10, wherein the late transition metal salt is $RuCl_3$; the weight:weight ratio of the compound of Formula (II) to $RuCl_3$ is from about 1:0.01 to about 1:0.2; the protic solvent comprises ethanol and water; the reaction is conducted at a temperature from about 65° C. to about 90° C.; and the compound of Formula (III) has a yield of at least about 60%.

21. The process of claim 17, further comprising a co-reactant selected from the group consisting of acetone, acetonitrile, 1-hexene, cyclohexene, $H_3PO_2$, $NaH_2PO_2$, and combinations thereof; and the weight:weight ratio of the compound of Formula (II) to the co-reactant is from about 1:0.005 to about 1:0.05.

22. The process of claim 20, wherein the optical activity of the compounds of Formulas (II) and (III) is (−), and the configuration of C-5, C-13, C-14, and C-9, respectively, is RSRR.

23. The process of claim 20, wherein the optical activity of the compounds of Formulas (II) and (III) is (+), and the configuration of C-5, C-13, C-14, and C-9, respectively, is SRSS.

* * * * *